United States Patent
Seo et al.

(10) Patent No.: US 11,679,554 B2
(45) Date of Patent: Jun. 20, 2023

(54) DEVICE FOR PRODUCING SKIN CARE PACK USING HYDROGEL, AND CONTROL METHOD THEREOF

(71) Applicants: Amorepacific Corporation, Seoul (KR); LINCSOLUTION CO., LTD., Siheung-si (KR)

(72) Inventors: Jeong Eun Seo, Yongin-si (KR); Ji Hoon Kim, Yongin-si (KR); Sung Won Yi, Yongin-si (KR); Seung Hoon Park, Incheon (KR); Keun Sik Choi, Seoul (KR)

(73) Assignees: AMOREPACIFIC CORPORATION, Seoul (KR); LINCSOLUTION CO., LTD, Siheung-si (KR)

( * ) Notice: Subject to any disclaimer, the term of this patent is extended or adjusted under 35 U.S.C. 154(b) by 423 days.

(21) Appl. No.: 16/650,693

(22) PCT Filed: Sep. 27, 2018

(86) PCT No.: PCT/KR2018/011468
§ 371 (c)(1),
(2) Date: Mar. 25, 2020

(87) PCT Pub. No.: WO2019/059746
PCT Pub. Date: Mar. 28, 2019

(65) Prior Publication Data
US 2020/0316858 A1 Oct. 8, 2020

(30) Foreign Application Priority Data
Sep. 25, 2017 (KR) .................. 10-2017-0123804

(51) Int. Cl.
*B29C 64/209* (2017.01)
*B33Y 30/00* (2015.01)
(Continued)

(52) U.S. Cl.
CPC .......... *B29C 64/209* (2017.08); *A45D 44/002* (2013.01); *A61K 8/0212* (2013.01);
(Continued)

(58) Field of Classification Search
CPC ......... B33Y 30/00; B33Y 50/02; B33Y 70/00; B33Y 80/00; B29C 64/393; B29C 64/106; A45D 44/002; A61K 8/0212; A61Q 19/00
See application file for complete search history.

(56) References Cited

U.S. PATENT DOCUMENTS

| 10,669,913 | B2 * | 6/2020 | Yamashita | ............. F02M 35/16 |
| 2017/0251713 | A1 * | 9/2017 | Warner | ................... A23P 30/20 |

FOREIGN PATENT DOCUMENTS

| CN | 106012052 A | 10/2016 |
| KR | 10-2000-0042715 A | 7/2000 |

(Continued)

OTHER PUBLICATIONS

Lee et al., Mask Pack Manufacturing Device With Mobile Terminal for the Skin Condition Check, Sep. 25, 2015, KR101556078 (English translation of description and original document).*

(Continued)

*Primary Examiner* — Philip C Tucker
*Assistant Examiner* — Evan T Hulting

(57) ABSTRACT

A device for producing a skin care pack using a hydrogel and to a control method thereof are disclosed. The device includes: a housing which is provided with a door for selectively opening and closing a work space for forming a skin care pack, and maintains a forming temperature required for producing the skin care pack; a platform having a base supported on a floor plate of the work space of the housing; a former including one or more nozzle modules which are provided to be movable in the work space and heat (Continued)

and discharge a hydrogel onto the platform; and a control unit for controlling the movement of the nozzle modules and the discharge of the hydrogel from the nozzle modules.

17 Claims, 13 Drawing Sheets

(51) Int. Cl.
    *B33Y 50/02*     (2015.01)
    *B33Y 70/00*     (2020.01)
    *B33Y 80/00*     (2015.01)
    *B29C 64/393*     (2017.01)
    *B29C 64/106*     (2017.01)
    *A45D 44/00*     (2006.01)
    *A61K 8/02*     (2006.01)
    *A61Q 19/00*     (2006.01)

(52) U.S. Cl.
    CPC ............ *A61Q 19/00* (2013.01); *B29C 64/106* (2017.08); *B29C 64/393* (2017.08); *B33Y 30/00* (2014.12); *B33Y 50/02* (2014.12); *B33Y 70/00* (2014.12); *B33Y 80/00* (2014.12)

(56) References Cited

FOREIGN PATENT DOCUMENTS

| | | |
|---|---|---|
| KR | 10-2014-0019656 A | 2/2014 |
| KR | 10-1556078 B1 | 9/2015 |
| KR | 10-1561476 B1 | 10/2015 |
| KR | 10-1668310 B1 | 10/2016 |
| KR | 10-2017-0070699 A | 6/2017 |

OTHER PUBLICATIONS

Lee, Gi Suk; Mask Pack Manufacturing Device With Mobile Terminal for the Skin Condition Check, English translation, Sep. 25, 2015, KR101556078.*

Park, Seok-Dal, Strip Salt Solution Rinsing Device Combined With Cleaning up Spray Nozzle, English translation, Jul. 15, 2000, KR1020000042715.*

International Search Report for PCT/KR2018/011468 dated, Jan. 7, 2019 (PCT/ISA/210).

Written Opinion of the International Searching Authority for PCT/KR2018/011468 dated Jan. 7, 2019 (PCT/ISA/237).

* cited by examiner

[FIG. 1]
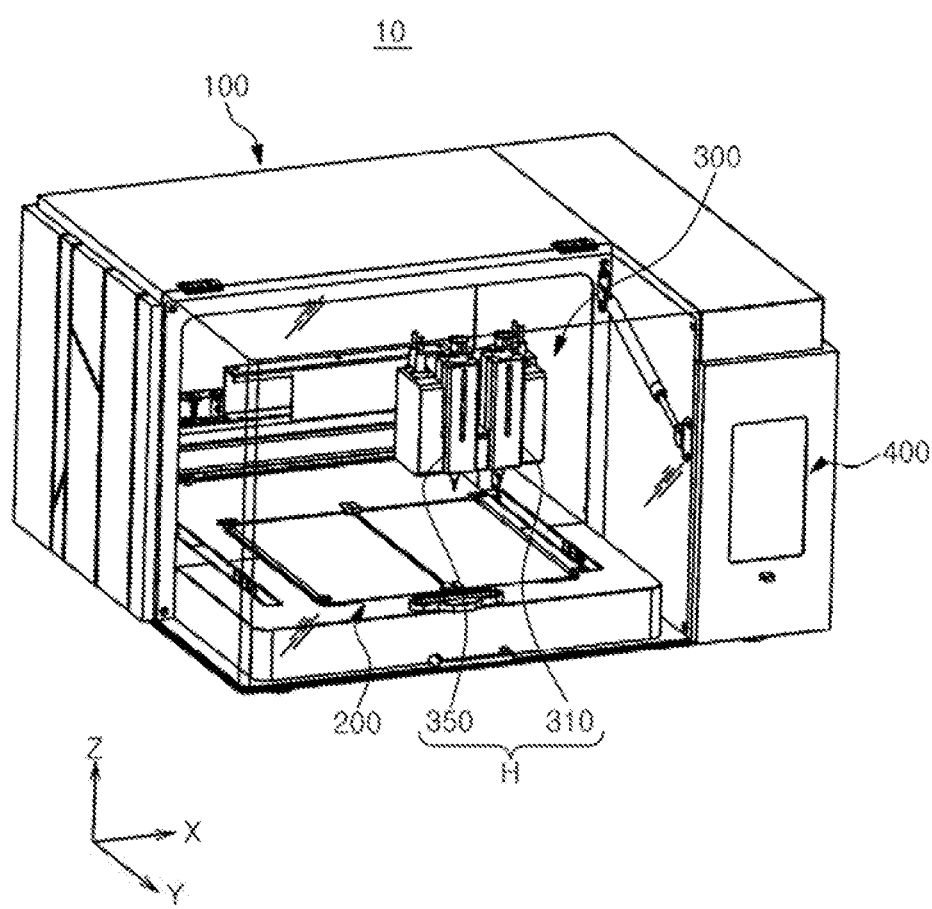

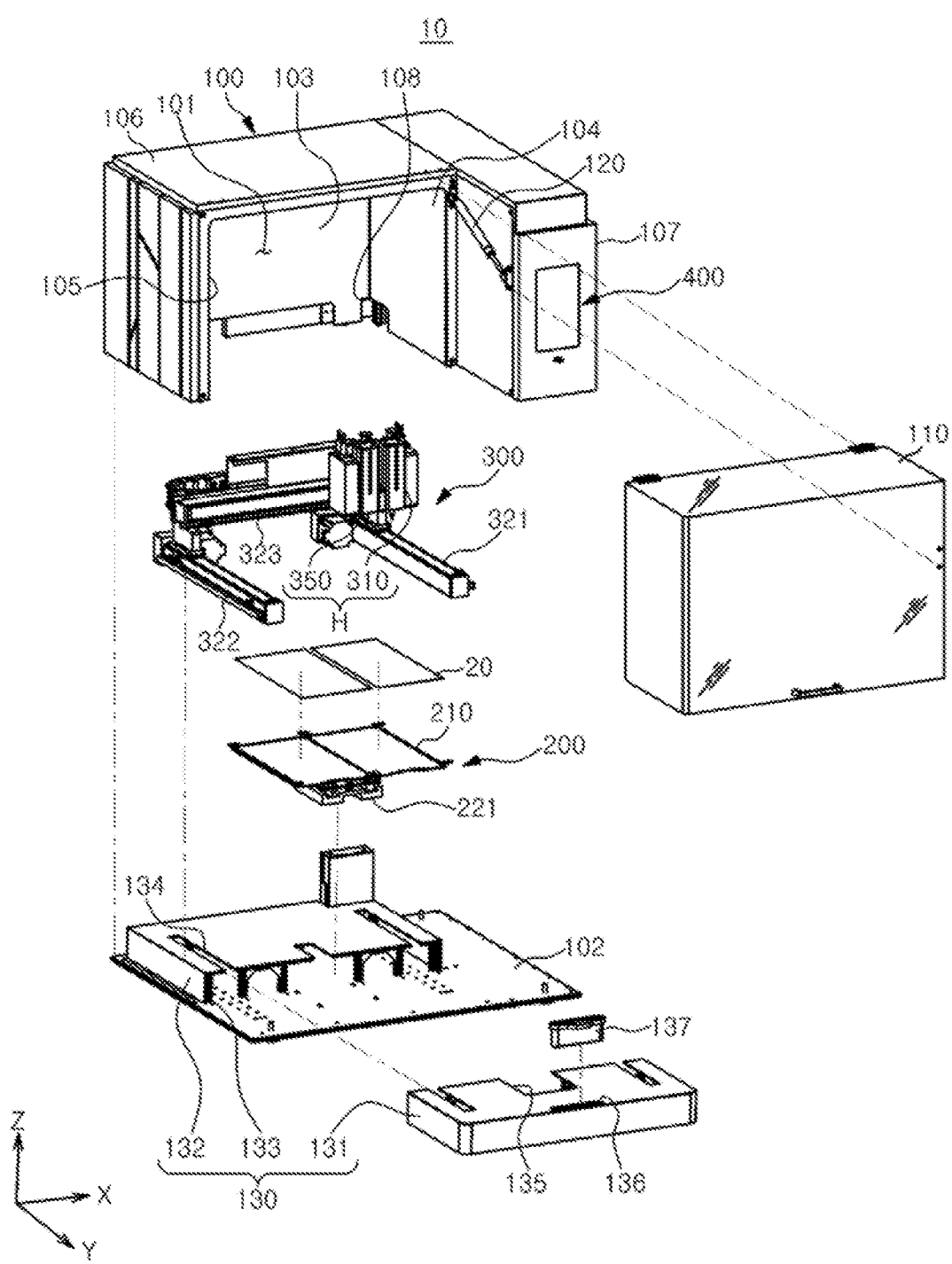
[FIG. 2]

[FIG. 3]
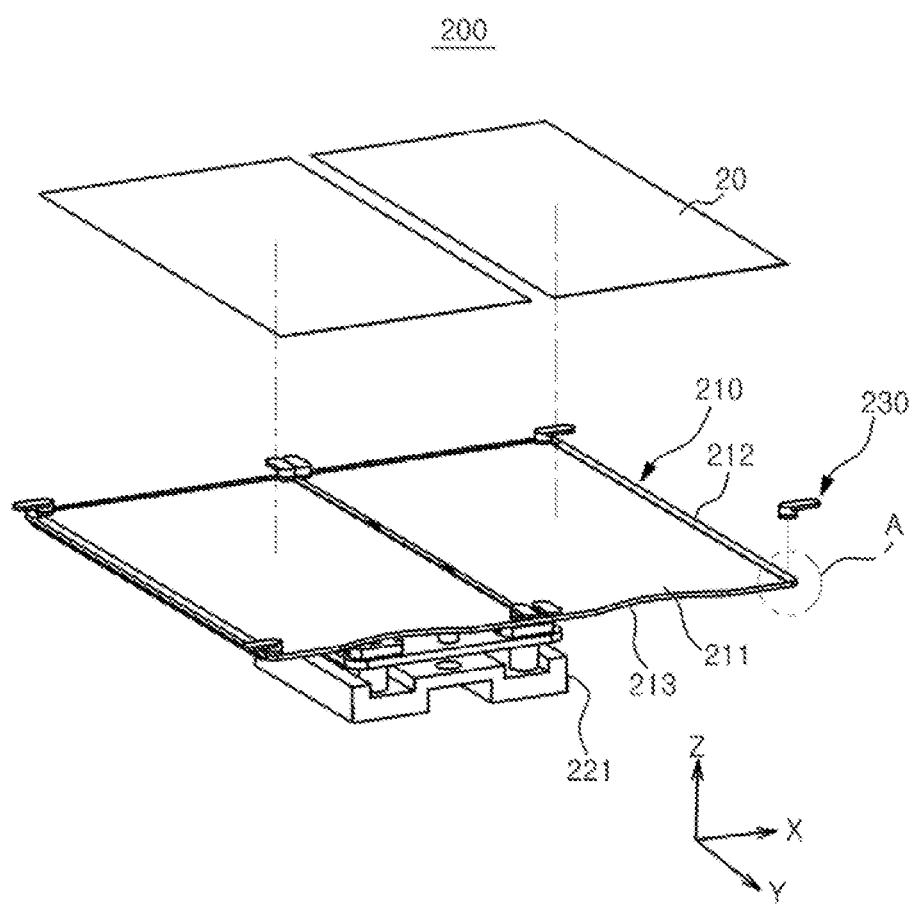

[FIG. 4]
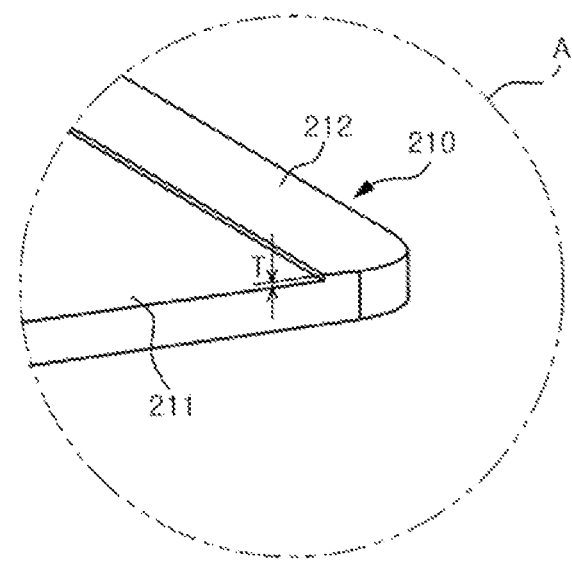

[FIG. 5]
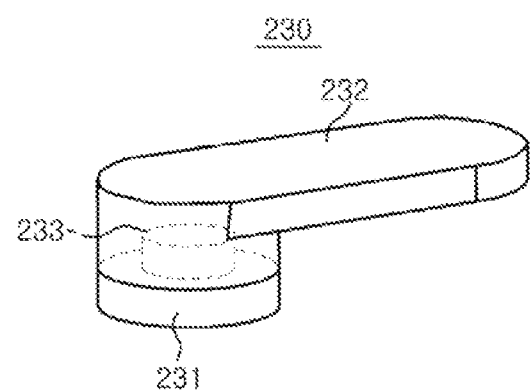

[FIG. 6]
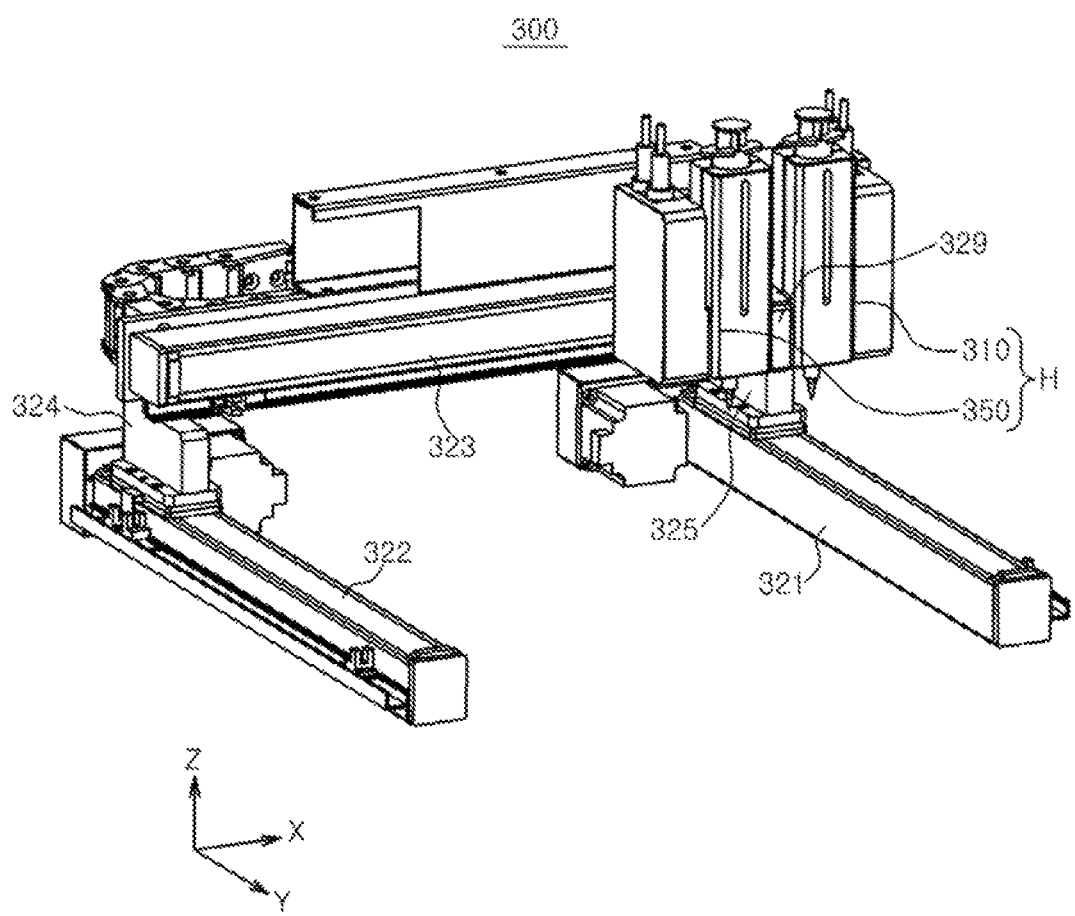

[FIG. 7]
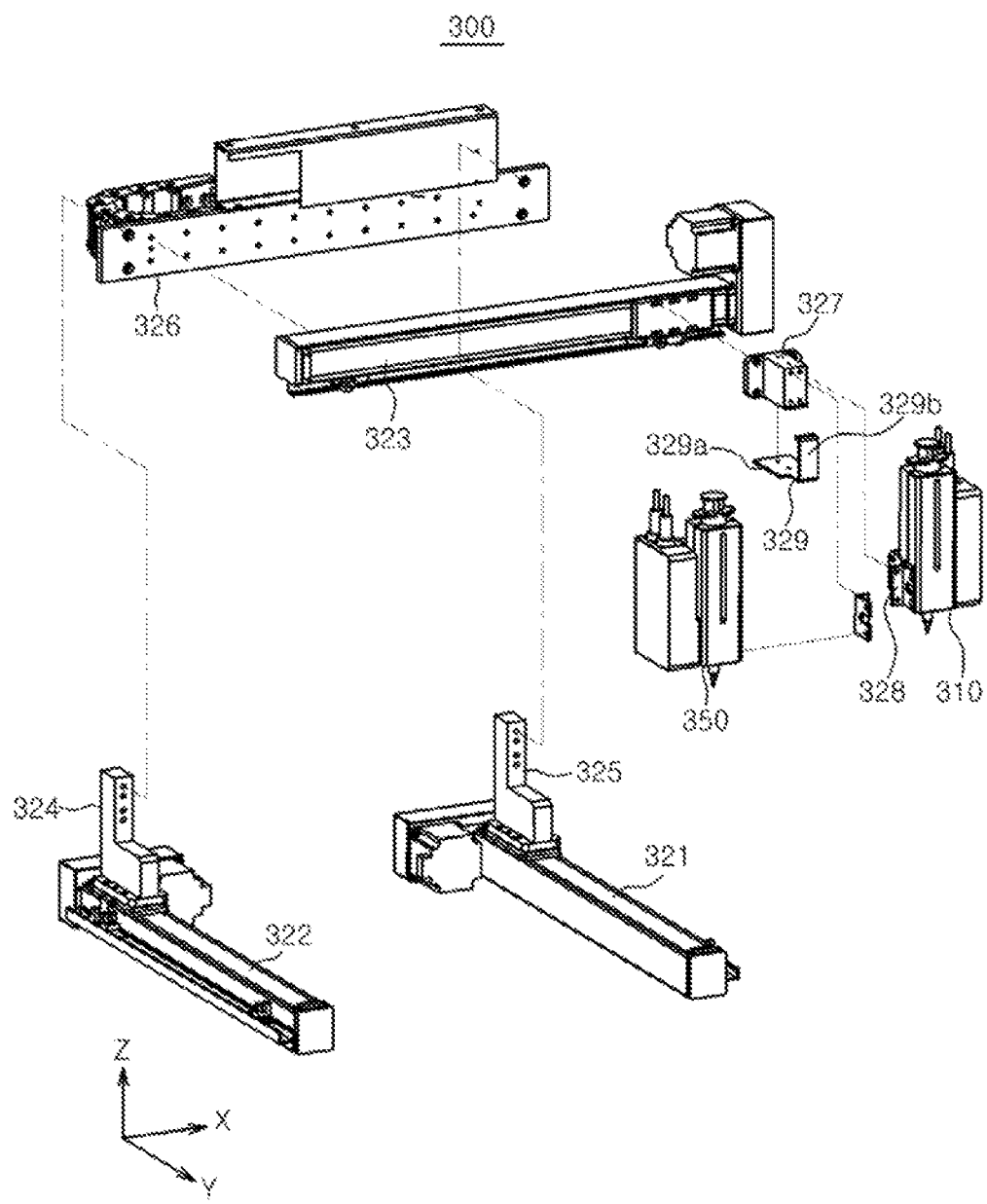

[FIG. 8]
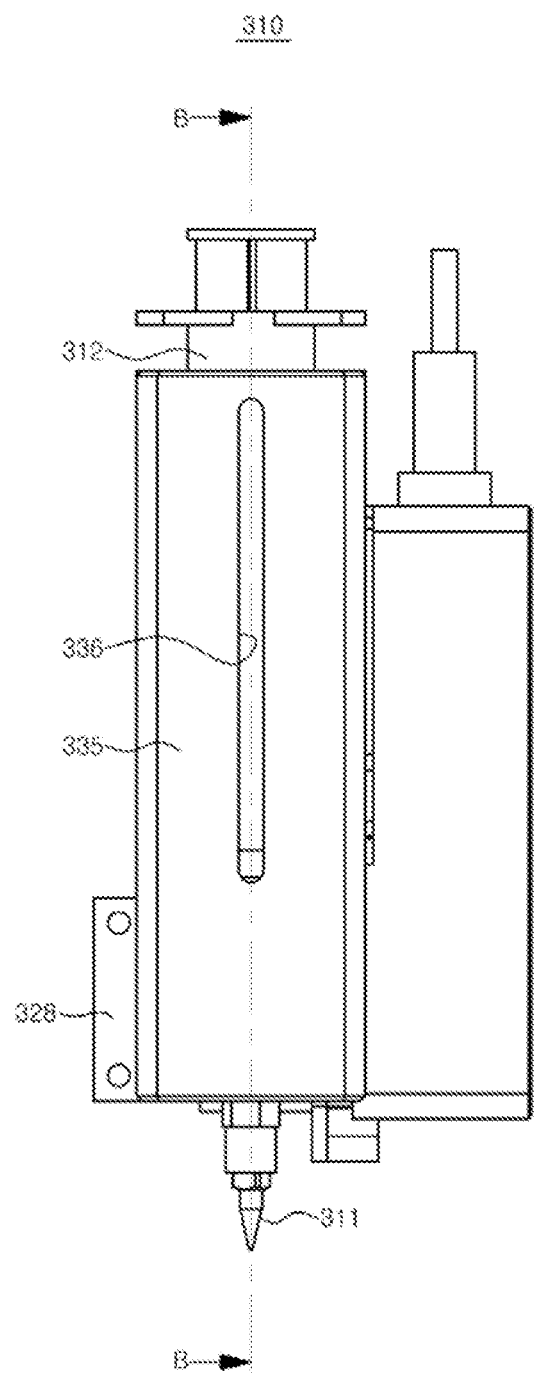

[FIG. 9]
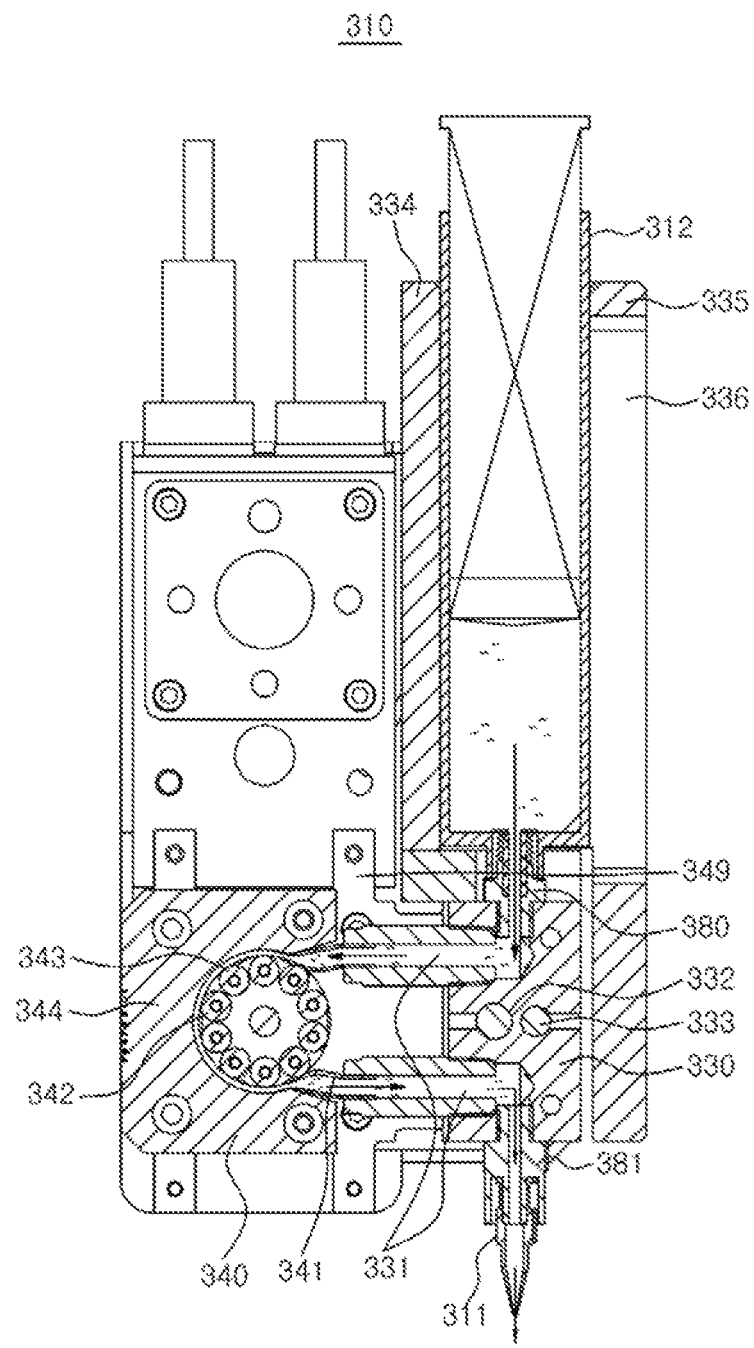

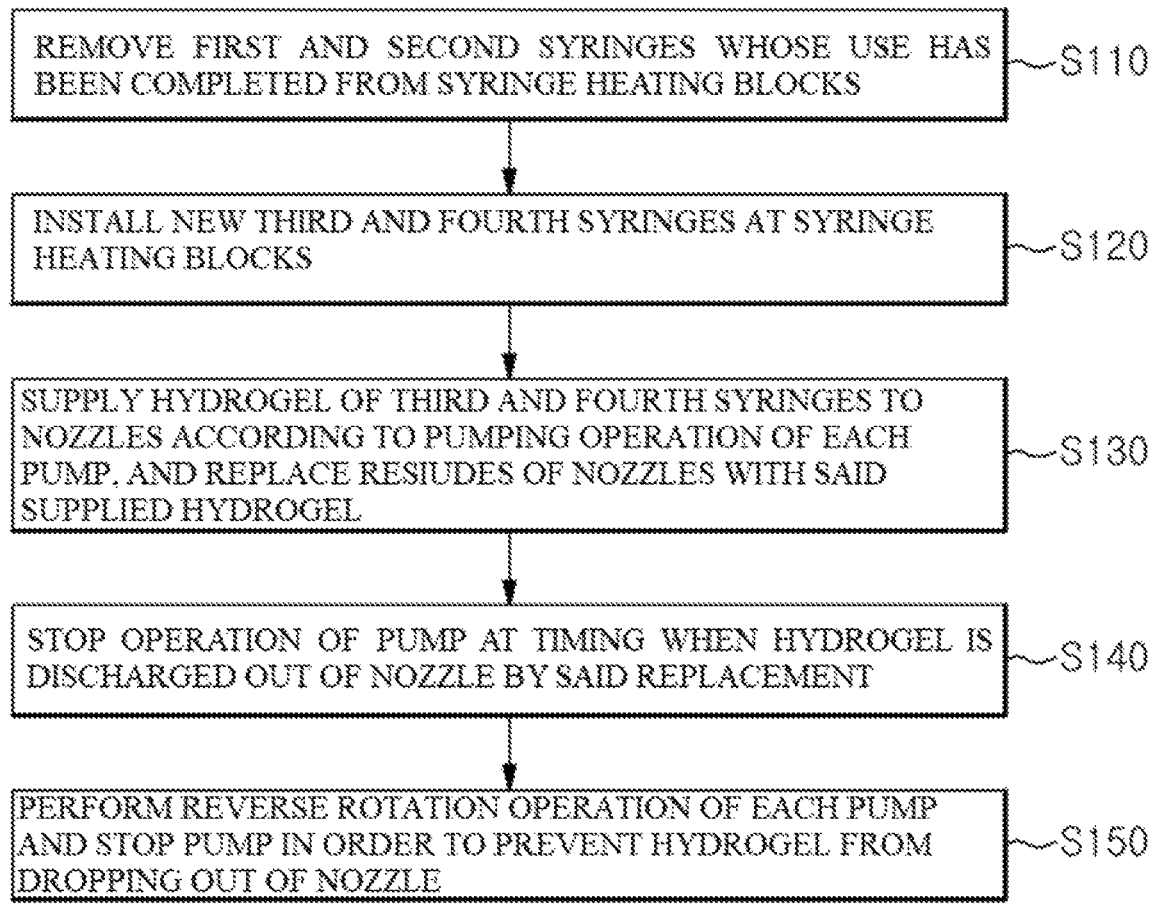

[FIG. 11]
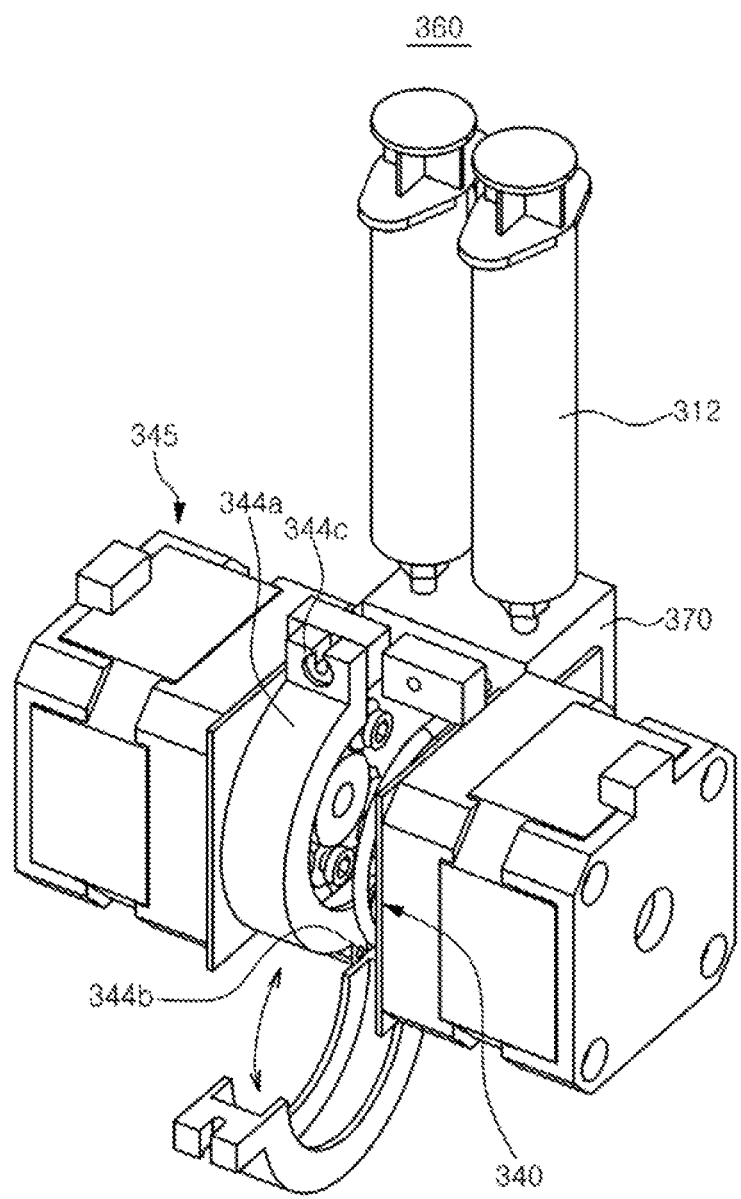

[FIG. 12]
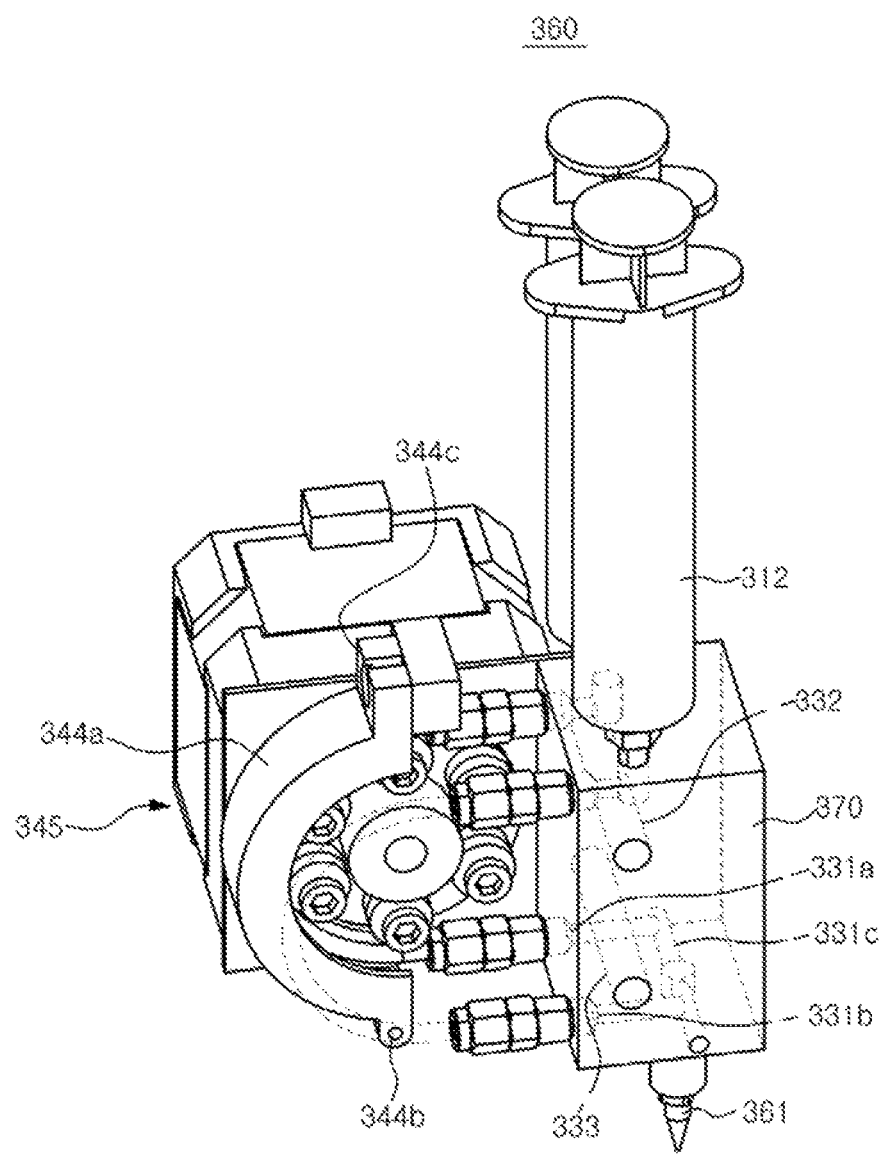

[FIG. 13]
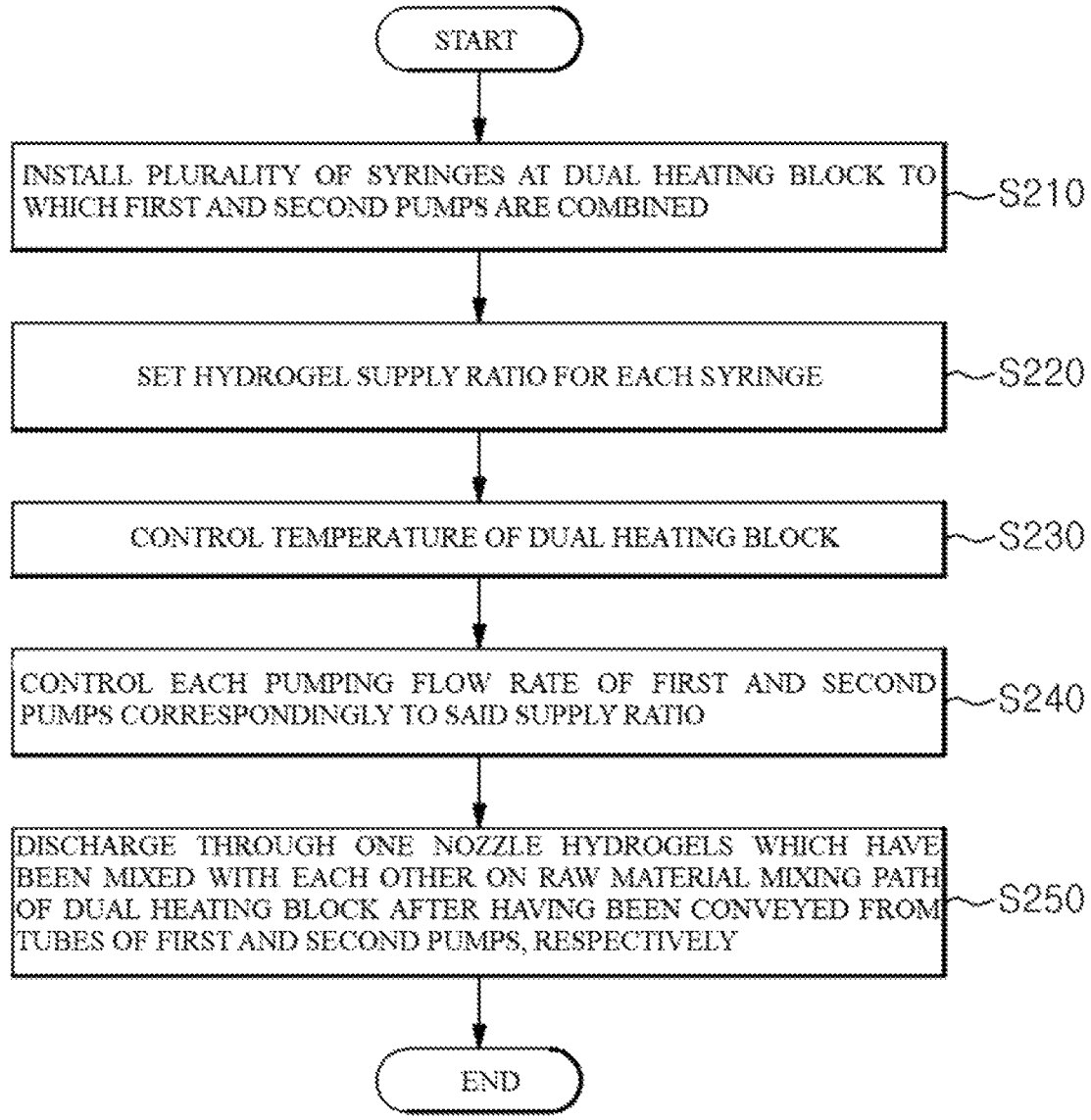

DEVICE FOR PRODUCING SKIN CARE PACK USING HYDROGEL, AND CONTROL METHOD THEREOF

CROSS REFERENCE TO RELATED APPLICATIONS

This application is a National Stage of International Application No. PCT/KR2018/011468 filed Sep. 27, 2018, claiming priority based on Korean Patent Application No. 10-2017-0123804, filed Sep. 25, 2017, the entire contents of which are hereby incorporated by reference.

TECHNICAL FIELD

The present invention relates to a device for producing a skin care pack using hydrogel, and a control method thereof.

BACKGROUND ART

In general, a mask pack is a kind of cosmetic which can relatively conveniently and effectively perform skin care such as skin winkle, skin elasticity, gloss or the like by supplying moisture and nutrition to skin.

Such mask pack may be tailored in view of a face contour and positions of eyes, a nose and a mouth on a face model basis for each year group of usual users. In addition, in the case of a three-dimensional mask pack, it may be constituted by a plurality of sheet parts so that it can closely contact each part of a face, such as a forehead, both chicks, nose, chin and the like.

The mask packs have various forms such as a sheet product of non-woven fabric material to which a liquid such as a skin lotion is applied, a mask pack product which improves wearing-feeling by having an essence contained within a fabric, such as cotton, a mask pack product which uses hydrogel, or a bio-cellulose mask pack product which uses a natural material. As the mask pack product using the hydrogel among these has an advantage that a functional component for skin care is selectively contained or mixed, demand for a hydrogel mask pack is increasing.

Meanwhile, a manufacturer mass-produces and supplies mask packs to the market using factory automation system which can produce a great number of mask packs for a short time period after determining a product standard based on a face model of a universal user for mass production. The mask packs supplied by mass-production are getting good response in the market because they exhibit their effects beyond a certain level at a relatively inexpensive price. But a user cannot use a mask pack which perfectly fits to his/her own skin due to the limit of mass production system. So, there is a drawback that a user cannot feel enough satisfaction with it.

Under this background, recently there have been trials to produce a custom-tailored mask pack. Specifically, there is suggested a technology which generates a 3D model of a user face, and produces a mask pack fit to a face shape of a user using it. This prior art is characterized by fabricating a base such as non-woven fabric or cotton based on modeled data so as to fit to a users face, or applying substance for skin care to a specific region of the base in view of a face shape of a user.

However, a device for producing the above-described customized, mask pack or a producing method is applicable to a mask pack having a base, but none of them can be applied to producing a hydrogel mask pack for which demand is increasing recently. That is because hydrogel is in a semi-solid state at a room temperature and thus is required to be heated for forming, which may lead to a drawback that, when the hydrogel is heated, its viscosity is decreased and the hydrogel leaks from a nozzle through which the hydrogel is discharged. That is, with the prior manner, it is very difficult or substantially impossible to precisely control a discharge timing, a discharge position and a discharge amount of the hydrogel in order to produce a customized mask pack.

Further, if the heating temperature of the hydrogel is lowered in order to prevent this problem, its viscosity enough for forming cannot be acquired, and thus there is no way except that productivity of a mask pack is extremely lowered or quality of the final product becomes very bad.

With regard to this, Korean patent application publication No. 10-2017-0070699 (Published on Jun. 22, 2017) provides "Manufacturing method of 3D-hydrpogel mask", and however, it is only intended to optimize the hydrogel contents, while still having the above-described problem. Thus, it cannot become a substantial countermeasure for producing the hydrogel mask pack.

Meanwhile, nowadays, as the interest in skin care increases, skin care products for each part of a physical body such as a hand, an arm, a foot, a leg or the like are being launched, and however, such skin care products also have the above-described problem. Therefore, there is an increasing need for a customized product and a product for which a raw material is the hydrogel.

DISCLOSURE

Technical Field

Embodiments of the invention provide a device for producing a skin care pack for which a raw material is hydrogel, and a control method thereof.

Additionally, embodiments of the invention provide a manufacturing device for producing a skin care pack rapidly and precisely in spite of using hydrogel as a raw material, and a control method thereof.

Further, embodiments of the invention provide a manufacturing device for producing a high quality hydrogel skin care pack and a control method thereof.

Also, embodiments of the invention provide a device for producing a skin care pack using hydrogel, which is optimized for body characteristics of a user, and, a control method thereof.

Technical Solution

According to an aspect of the present invention, there is provided a device for producing a skin care pack using hydrogel, the device comprising: a housing which is provided with a door for selectively opening and closing a work space for forming a skin care pack, and which maintains a forming temperature required for producing the skin care pack; a platform having a base supported on a floor plate of the work space of the housing; a former including one or more nozzle modules which are provided to be movable in the work space, and which heat the hydrogel and discharge same onto the platform, and a control unit for controlling movement of the nozzle modules and discharge of the hydrogel from the nozzle modules, wherein the nozzle module includes: a main block which includes a heater, and which is formed of a thermally conductive material; a syringe which is installed at the main block, and which stores the hydrogel; a nozzle which is installed at the main block, and which discharges the hydrogel onto the platform: and a pump which is installed at the main block, and which supplies the hydrogel from the syringe to the nozzle.

Further, there is provided, a device for producing; a skin care pack using hydrogel, wherein the door is hinge-combined to a ceiling wall of the housing, and there is provided a tension gas spring between the door and a side wall of the housing.

Further, there is provided a device for producing a skin care pack using hydrogel, wherein the housing includes a driving device protection cover which is installed on the floor plate of the housing so as to cover a lower portion of a linear driving device of the platform or a lower portion of a linear driving device of the former, and wherein the driving device protection cover is provided to be capable of being assembled or disassembled for installation and maintenance of the platform or the former.

Further, there is provided a device for producing a skin care pack using hydrogel, wherein a residue collecting receptacle for collecting residues which are generated when washing the nozzle of the former is detachably installed at a front portion of the driving device protection cover.

Further, there is provided a device for producing a skin care pack using hydrogel, wherein the platform includes: a z-axis linear driving device which is driven according to a control signal supplied by the control unit, and which is installed on the floor plate of the housing; a base which is ascended or descended along a z-axis direction by the z-axis linear driving device, which is disposed above a driving device protection cover of the work space of the housing, and which has a plurality of film seat portions partitioned by a peripheral stepped portion so that a pattern part constituting a mask pack may be dividedly formed into a plurality of pieces; and a plurality of film holders which are attached to or detached from the peripheral stepped portion of the base by a means of magnetic force.

Further, there is provided a device for producing a skin care pack, using hydrogel, wherein the hydrogel stored in the syringe receives heat transferred front the heater, so that its viscosity is maintained between 120 CPS and 2,500 CPS.

Further, there is provided a device for producing a skin care pack using hydrogel, wherein the syringe, the nozzle, and the pump are heated by heat transferred to themselves from the heater.

Further, there is provided a device for producing a skin care pack using hydrogel, wherein the nozzle and the pump include thermally conductive metal as a material so that they can be heated by heat conduction transferred to themselves through the main block.

Further, there is provided a device for producing a skin care pack using hydrogel, wherein the syringe is disposed at a gravity-direction upper side of the main block, the pump is disposed at a lateral one side of the main block, and the nozzle is disposed at a gravity-direction lower side of the main block.

Further, there is provided a device for producing a skin care pack using hydrogel, wherein the heater heats the syringe, the nozzle and the pump so that viscosity of the hydrogel discharged from the nozzle is maintained between 120 CPS and 2,500 CPS, or so that temperature of the hydrogel is maintained between 70° C. and 95° C.

Further, there is provided a device for producing a skin care pack using hydrogel, wherein the main block includes a raw material flow path which provides to the pump the hydrogel supplied from the syringe, and which provides to the nozzle the hydrogel supplied from the pump, and the raw material flow path is heated by the heater.

Further, there is provided a device for producing a skin care pack using hydrogel, wherein the main block is further provided with a temperature sensor for sensing temperature of the main block, and the control unit controls the heater so that temperature of the main block measured at the temperature sensor is maintained to a predetermined temperature range.

Further, there is provided a device for producing a skin care pack using hydrogel, wherein the nozzle module further includes: a syringe heating block which is extended upward from an upper surface periphery of the main block, and which has a first semi-circular recessed portion in contact with an outer circumferential surface of a side of the syringe; and a syringe cover block which is disposed opposite the syringe heating block with respect to the syringe, and which has a second semi-circular recessed portion in contact with an outer circumferential surface of another side of the syringe.

Further, there is provided a device for producing a skin care pack using hydrogel, wherein a slit for checking a raw material remainder quantity of the syringe is formed in the syringe cover block.

According to another aspect of the present invention, there is provided a device for producing a skin care pack using hydrogel, the device comprising: a housing which is provided with a door for selectively opening and closing a work space for forming a skin care pack, and which maintains a forming temperature required for producing the skin care pack; a platform having a base supported on a floor plate of the work space of the housing; a former including one or more nozzle modules which are provided to be movable in the work space, and which heat the hydrogel and discharge same onto the platform; and a control unit for controlling movement of the nozzle module and discharge of the hydrogel from the nozzle module, wherein the platform includes: a z-axis linear driving device which is driven according to a control signal supplied by the control unit, and which is installed on the floor plate of the housing; a base which is ascended or descended along a z-axis direction by the z-axis linear driving device, which is disposed above a driving device protection cover of the work space of the housing, and which has a plurality of film seat portions partitioned by a peripheral stepped portion so that a pattern part constituting a mask pack may be dividedly formed into a plurality of pieces; and a plurality of film holders which are attached to or detached from the peripheral stepped portion of the base by a means of magnetic force, and wherein the film holder includes: a pad which contacts an upper surface of the film and the peripheral stepped portion of the base in order to prevent scratch generation resulting from the contact with the film placed on the film seat portion; a handle connected to a top of the pad; and a magnet disposed in the handle with respect to an upper side position of the pad.

According to another aspect of the present invention, there is provided a device for producing a skin care pack using hydrogel, the device comprising: a housing which is provided with a door for selectively opening and closing a work space for forming a skin care pack, and which maintains a forming temperature required for producing the skin care pack; a platform having a base supported on a floor plate of the work space of the housing; a former including one or more nozzle modules which are provided to be movable in the work space, and which heat the hydrogel and discharge same onto the platform; and a control unit for controlling movement of the nozzle module and discharge of the hydrogel from the nozzle module, wherein the former includes: two y-axis linear driving devices which are parallelly disposed on the floor plate of the housing except an installation area of the platform; two adapter blocks combined to moving plates of the y-axis linear driving devices, respectively; an x-axis linear driving device installed between the adapter blocks; and a mount block combined to a moving plate of the x-axis linear driving device, and wherein the nozzle modules are fixed to the mount block and moved together with the mount block.

Further, there is provided a device for producing a skin care pack using hydrogel, wherein the mount block has a shape of T, and the nozzle modules are symmetrically disposed at both sides of the mount block.

Further, there is provided a device for producing a skin care pack using hydrogel, wherein the nozzle modules and the mount block are connected to each other through an angle member of an L-shaped cross section, the former further includes a finishing member which is combined to a lower surface of the mount block for a finishing process of the angle member disposed between the nozzle modules, and the finishing member includes: a fixed plate in contact with the lower surface of the mount block; and a finishing plate which is extended from the fixed plate so as to have a C-shaped cross section, so that it is disposed between the nozzle modules while covering a front position of the angle member.

According to another aspect of the present invention, there is provided a device for producing a skin care pack using hydrogel, the device comprising: a housing which is provided with a door for selectively opening and closing a work space for forming a skin care pack, and which maintains a forming temperature required for producing the skin care pack; a platform having a base supported on a floor plate of the work space of the housing; a former including one or more nozzle modules which are provided to be movable in the work space, and which heat the hydrogel and discharge same onto the platform; and a control unit for controlling movement of the nozzle module and discharge of the hydrogel from the nozzle module, wherein the nozzle module is a dual nozzle module which is controlled by a control unit to operate in linkage with the platform, and which discharges a mixed raw material for forming a mask pack while being moved or stopped by a y-axis linear driving device and an x-axis linear driving device, a dual heating block is mounted on the dual nozzle module, as a first pump part and a second pump part of the dual nozzle module operate, raw materials corresponding to different or same pumping flow rate are supplied to a raw material mixing path of the dual nozzle module, and mixed therein to make the mixed raw material, and the mixed raw material is discharged onto a film of the platform through one nozzle connected to the raw material mixing path so as to make a pane portion corresponding to a mask pack.

According to another aspect of the present invention, there is provided a control method of a device for producing a skin care pack in which a control unit controls a relative movement of a platform on which a skin care pack is formed and a former which discharges hydrogel heated, wherein the hydrogel is discharged toward the platform through at least one nozzle module of the former, the control method comprising: after separating from the nozzle module a syringe whose use has been completed or replacement is necessary, installing a new syringe to the nozzle module; receiving an input of a washing instruction; and replacing residues stayed in the nozzle module with the hydrogel of the new syringe by driving a pump mounted on the nozzle module and supplying the hydrogel of the new syringe to a nozzle of the nozzle module, wherein the replacing includes: driving the pump by the control unit until a timing when the hydrogel of the new syringe is discharged through the nozzle on the basis of information calculated according to a structural characteristic of a path through which the hydrogel is moved in the nozzle module and operation condition of the pump; and stopping the pump by the control unit after its reverse rotation in order to prevent the hydrogel from dropping out of the nozzle.

Advantageous Effects

According to a device for producing a skin care pack using hydrogel and a control method thereof according to the embodiments of the present invention, there is an effect of being capable of producing a skin care pack for which a raw material is the hydrogel.

Further, there is an advantage of producing a skin care pack rapidly and precisely even though using hydrogel as a raw material.

In addition, there is an advantage of being capable of producing a high quality a hydrogel skin care pack.

Further, there is an advantage of being capable of producing a skin care pack using hydrogel, which is optimized for body characteristics of a user.

DESCRIPTION OF DRAWINGS

FIG. 1 is a perspective view of a device for producing a skin care pack using hydrogel according to an embodiment of the invention.

FIG. 2 is an exploded perspective view of the device for producing a skin care pack using hydrogel shown in FIG. 1.

FIG. 3 is a perspective view showing a shaping platform and a film shown in FIG. 2.

FIG. 4 is an enlarged perspective view of a circle A shown in FIG. 3.

FIG. 5 is a perspective view for explaining a configuration of a film holder shown in FIG. 4.

FIG. 6 is a perspective view showing the former shown in FIG. 2.

FIG. 7 is an exploded perspective view of the former shown in FIG. 6.

FIG. 8 is a front view of the nozzle module disposed at a right side of the discharge unit of the former shown in FIG. 7.

FIG. 9 is a cross-sectional view taken along line B-B shown in FIG. 8.

FIG. 10 is a flowchart for explaining a washing process, which is a control method of the device for producing a skin care pack using hydrogel according to the invention.

FIG. 11 is a perspective view of a dual nozzle module of a device for producing a skin care pack using hydrogel according to an application example of the invention.

FIG. 12 is a perspective view for explaining operational relation of the dual nozzle module shown in FIG. 11.

FIG. 13 is a flowchart for explaining a control method of the dual nozzle module shown in FIG. 12.

BEST MODE

Hereinafter, specific exemplary embodiments of the invention will be described in detail, with reference to the drawings.

Additionally, it is noted that in the description of the invention, the detailed description for known related configurations or functions may be omitted when it is deemed that such description may obscure essential points of the invention.

FIG. 1 is a perspective view of a device for producing a skin care pack using hydrogel according to an embodiment of the present invention; and FIG. 2 is an exploded perspective view of the device for producing a skin care pack using hydrogel shown in FIG. 1. Further, FIG. 3 is a perspective view showing a shaping platform and film shown in FIG. 2; FIG. 4 is an enlarged perspective view of a circle A shown in FIG. 3, and FIG. 5 is a perspective view for explaining a configuration of a film holder shown in FIG. 4.

Referring to FIGS. 1 and 2, a device 10 for producing a skin care pack using hydrogel according to an embodiment of the invention includes a housing 100, a platform 200, a former 300 and a control unit 400.

In the embodiment, as a device that is intended to produce a skin care pack for which a raw material is hydrogel and which may be attached to the skin for use by a user, a device 10 for producing a skin care pack using the hydrogel may produce a skin care pack based on modeling data for any body part such as a face, a hand, an arm, a foot, a leg or the like of the user. In the embodiment and the description blow, the skin care pack using the hydrogel is described by way of example as being a mask pack which is for attachment to a user's face, but the technical idea of the invention is not limited to this.

The housing 100 may be provided with a work space 101 which becomes a movement space of a discharge unit H for forming a mask pack, and a door 110 which selectively opens and closes the work space 101. The housing 100 may be configured to maintain a forming temperature required for producing a mask pack in a state where the door 110 is closed.

On a lower front position of the door 110 spaced away from a hinge of the door 110, a door handle is installed. A user may easily open or close the door 110 by holding the handle and rotating the door 110.

The platform 200 has a base 210 which is supported on a floor plate 102 of the work space 101 of the housing 100, and whose movement in a vertical direction is controlled.

The former 300 may be disposed in the work space 101 of the housing 100 with respect to an upper position of the platform 200. The former 300 may discharge onto the platform 200 a raw material for forming a mask pack. For example, the former 300 functions to form a mask pack on the film 20 by discharging a raw material onto the film 20 which is supportable by or separable from the base 210 of the platform 200. Here, the raw material may be in a heating condition state, for example, in a state where it is heated to a level of about 90° C., within the nozzle modules 310, 350 of the discharge unit H. The heating condition may be set by the control unit 400 and controlled through a temperature sensor. For the purpose of this, a heater and a temperature sensor may be mounted on the former 300 as described below.

In the embodiment, a raw material or a mixed raw material which is capable of being stored in a cartridge (not shown) or a syringe and discharged by pumping in order to form a custom-tailored mask pack, and the raw material may be one which has properties as a semisolid substance or gel at room temperature, but which, when it is heated, has properties as a liquid while its viscosity decreases below a certain level.

For example, the raw material may maintain a viscosity ranging from 120 CPS to 2,500 CPS at a temperature ranging from 70° C. to 95° C., which enables the discharge through the nozzle. However, if it is heated to 100° C. or higher, a problem that water which is one of components of the raw material is evaporated may occur. So, it is preferable to set the temperature of the raw material to be 95° C. or lower for the purpose of safety. Specifically, the raw material may be any one of hydrogel, gel type synthetic resin and a material which contains a raw material for a functional cosmetic in polymer, and in the embodiment, it is described by way of example as being the hydrogel.

The control unit 400 may be electrically connected to the platform 200 and the former 300 through various electric cables, and control electrical configurations of the platform 200 and the former 300.

The control unit 400 may include an input/output display device (e.g., a touch screen), an electronic circuit device and a power supply connected thereto.

The control unit 400 may further include a USB port (not shown) for inputting and outputting external data. The control unit 400 may control operation of the former 300 and the platform 200, receive the input of setpoints required for forming a mask pack and custom-tailored model CAD data, and display an operation state. In addition, the control unit 400 may be disposed on a side portion of the housing 100.

In this regard, the control unit 400 may calculate or set a movement path of the former 300, a discharge speed, a discharge amount, a discharge timing of hydrogel or the like for forming a mask pack. That is, the control unit 400 controls the discharge of the hydrogel at the nozzle modules 310, 350. Basic data for this may be transmitted from the outside through wired/wireless data communication, or through a storage means such as a USB or the like.

Further, the control unit 400 may have a temperature control algorithm by which a raw material forming temperature or heater operation temperature of the former 300, or an operation temperature of a platform heater (not shown) attached to a lower surface of the base 210 of the platform 200 is feedback controlled from a corresponding temperature sensor.

For example, a measuring target of the temperature sensor may be temperature of a main block of each nozzle module 310, 350 of the former 300. If a target temperature of the hydrogel is 90° C., a setting temperature value of the main block may be set to a range higher than the target temperature. For example, the setting temperature value of the main block may be a predetermined range between 91° C. and 93° C.

The device 10 for producing a skin care pack using hydrogel of the embodiment may take a driving type of a Cartesian type 3D printer which has an optimal structure so as to produce a hydrogel mask pack based on raised temperature forming. Further, the device 10 for producing a skin care pack using the hydrogel is configured to discharge a raw material in an extruding method by a pump such as a peristaltic pump. The device 10 for producing a skin care pack using the hydrogel of the embodiment may include a detailed configuration to be described later for rapidly and accurately embodying customized mask pack production.

For example, the housing 100 may have a box-shaped wall structure. The housing 100 may be surrounded by exterior material suitable for a cosmetic producing device, and be provided with a thermal insulating material (not shown) installed within the wall as an interior material.

As shown in FIG. 2, the housing 100 includes a rear wall 103 which is assembled or erected on the floor plate 102 so as to correspond to a boundary position of the work space

101. A power connector (not shown) connected to a power source terminal of the control unit 400 may be installed behind the rear wall 103.

Further, the housing 100 may include a pair of side walls 104, 105 which are connected to both sides of the rear wall 103 and erected on the floor plate 102. Also, the housing 100 may include a ceiling wall 106 connected to upper ends of the pair of side walls 104, 105 and the rear wall 103, and the front of the housing 100 may be opened. Here, the floor plate 102 of the housing 100 may be combined to lower surfaces of the rear wall 103 and the side walls 104, 105 by using a plurality of bolts.

Further, in order to replace the syringe or take out a mask pack, the front of the housing 100 and the work space 101 may be selectively closed or opened correspondingly to opening and closing operation of the door 110 (e.g., rotation around a rotational axis of an x-axis direction). For the purpose of this, the housing 100 may include a tension gas spring 120 installed between the door 110 hinge-combined to the ceiling wall 106, and a front surface of the side surface 104. The tension gas spring 120 functions to maintain an open state of the door 110 by supporting it at the time of rotational opening of the door 110, or to help the door 110 to be opened and closed smoothly. Further, the tension gas spring 120 may damp a shock at the time of closing of the door 110.

Also, the housing 100 may include a control unit casing 107 which is integrally connected to an outer side of the right side wall 104, and which exposes an input/output display device of the control unit 400 to the front direction of the housing 100.

The control unit casing 107 may be a control box including a power supply device, an electronic circuit device for control, or the like. In addition there may be a cable passage 108 on the right side wall 104 of the housing 100 for spatially connecting an inner space of the control unit casing 107 and the work space 101 to each other.

Further, the housing 100 may include a driving device protection cover 130 installed at the floor plate 102 of the housing 100 so as to cover a lower portion of a linear driving device 221 of the platform 200 and a lower portion of linear driving devices 321, 322, 323 of the former 300.

The driving device protection cover 130 may be a cap structure having partially penetrated areas 134, 135, and may prevent a portion of raw material or foreign material from entering a rail or operation region of the linear driving devices 321, 322, 323 and causing a device failure.

For the purpose of this, parts located at lower portions of the y-axis linear driving devices 321, 322 and the z-axis linear driving device 221 may be placed in an inner space of the driving device protection cover 130. Contrarily, moving parts of the y-axis linear driving devices 321, 322 and the z-axis linear driving device 221, and payload objects loaded on the moving parts thereof (e.g., the base 210, the x-axis linear driving device 323, the discharge unit H) may be placed above the driving device protection cover 130 through the penetrated areas 134, 135 formed on an upper surface of the driving device protection cover 130.

Further, in a lower surface of the driving device protection cover 130, a plurality of bolt holes (not shown) may be formed for being combined to bolts installed or floor plate 102.

Also, the driving device protection cover 130 may be constituted by a front cover portion 131 and a rear cover portion 132 which can be assembled or disassembled for installation and maintenance of the platform 200 or the former 300.

On both cover wall portions at which the front cover portion 131 and the rear cover portion 132 confront to each other, a recessed portion or a protruding portion 133, such as concave and convex shapes, which can be engaged to each other, may be formed. As a result, the engagement and contact between the front cover portion 131 and the rear cover portion 132 can be made tightly.

In particular, the front cover portion 131 of the driving device protection cover 130 may include a residue collecting receptacle 137 with a mouth portion opened toward the z-axis direction for collecting residues which are generated when washing the nozzle of the former 300. Specifically, an installation hole 136 may be formed on the upper surface of the front cover portion 131. The residue collecting receptacle 137 may be detachably inserted or installed into the installation hole 136.

As a user can separate and wash the residue collecting receptacle 137, it is possible to perform maintenance and maintain cleanness with ease. Further, nozzle clogging resulting from replacement of a raw material may be prevented in advance.

Referring to FIGS. 2 to 4, the platform 200 may include the z-axis linear driving device 221 which is installed on the floor plate 102 of the housing 100, and which is driven according to a control signal provided from the control unit 400. In the embodiment, the z-axis linear driving device 221 is described by way of example as being provided on the platform 200 for 3D printing, but the z-axis linear driving device 221 may be provided on the former according to an embodiment.

Also, the platform 200 includes the base 210 which is ascended or descended along the z-axis direction by the z-axis linear driving device 221, and which is disposed above the driving device protection cover 130 of the work space 101 of the housing 100, and a plurality of film holders 230.

Material of the base 210 may be stainless steel (e.g., SUS 430 series material) and have a rust-resistant function, and there is an advantage that the film holder 230 can be attached thereto by means of a magnetic force based on properties of SUS 430 series material.

There may be further provided an electrostatic removing device (not shown), which is installed above the base 210 with the rear wall 103 of the housing 100 or the like as a supporting base. Here, the electrostatic removing device may be constituted by an ion gun and a foreign substance blowing device, so that, by removing electrostatic from the film 20 by irradiating ions toward the film 20, it is possible to prevent dust or micro foreign matters from being attached to the film 20 and relatively big foreign substances can be removed by a fluid force of the blowing device. Therefore, it is possible to form a pattern part of a hydrogel mask pack having no foreign substance or dust on the film 20, and thus it is possible to produce a high quality mask pack. That is, according to the embodiment, it is possible to provide a custom-tailored skin care, pack using hydrogel which is constituted by the pattern part that is divided into a plurality of pieces correspondingly to a three-dimensional face shape of a user.

Meanwhile, there is also a case where a mask pack is constituted by two segments correspondingly to upper and lower portions of a user's head. In order to perform the production of such mask pack with ease, the base 210 may have a film seat portion 211 which is partitioned into a plurality of pieces by a peripheral stepped portion 212 so that the pattern part (not shown) constituting a mask pack may be dividedly formed into a plurality of pieces, and separate films 20 may be placed on the film seat portions 211, respectively. Here, a step height T of the peripheral stepped portion 212 may be the same as a thickness of the film 20, and, for example, the step height T may be 0.2t (where t is 1 mm).

In this regard, a front portion of the base 210 may have no peripheral stepped portion 212 so as to be opened. That is, the peripheral stepped portion 212 may have a shape of English alphabet E with respect to a planar shape of the base 210, and is integrally formed with respect to an upper surface periphery of the base 210.

For example, the film seat portion 211 may be formed into two planar rectangular shapes. In this case, a semi-circular or semi-elliptical film removal recessed portion 213 is formed in a front portion of each film seat portion 211, so that, when user's fingers enter partially, they can easily grip and pull a periphery of the film 20.

When a user locates the film 20 at a correct position or grips the film 20 after a mask pack has been formed, interference between a user's hand and the base 210 may not take place thanks to the film removal recessed portion 213, and thus it is possible for the user to easily separate or remove the film 20 from the film seat portion 211.

Referring to FIGS. 4 and 5, each film holder 230 may be attached to or detached from the peripheral stepped portion 212 of the base 210 by means of a magnetic force, and can bring the film 20 into close contact with the film seat portion 211 by means of its weight or a magnetic force. The film holder 230 may be provided in plural, and as one example, four film holders may be provided for each film seat portion 211, so that they can fix each corner of the film 20 to the base 210.

Material of a body of the film holder 230 may be aluminum material (e.g., AL 6061 series material). Therefore, the film holder 230 can be lightweight, thus enabling easy manipulation and handling of the film holder 230. A surface of the film holder 230 may be post-treated by white anodizing, which can lead to increase in the durability and lifespan of the film holder 230 that can be transferred by a user's hand.

In order to prevent scratch generation or damage of the film 20 resulting from the contact of the film holder 230 with the film 20 placed on the film seat portion 211, each film holder includes a pad 231 which contacts an upper surface of the film 20 and the peripheral stepped portion 211 of the base 210. The pad 231 may be relatively soft cushion material, such as silicone material or rubber material, when compared to a handle 232.

Further, each film holder 230 includes the handle 232 of a cramp structure, which is connected to a top of the pad 231, and a magnet 233 disposed inside the handle 232 with respect to upper position of the pad 231. The magnet 233 may be a permanent magnet or a neodymium magnet. There are advantages that each film holder 230 can be attached to or detached from the base 210 using a magnetic force of the magnet 233, and that attachment location on the base 210 can be changed. The film holder 230 can be redesigned into various shapes and structures as long as it has a handle shape.

A user may fit and insert the film 20 to the film seat portion 211 inside the peripheral stepped portion 212, and fix the film 20 with the film holder 230. A planar size of each film 20 may be formed so as to be relatively small compared to an area of the film seat portion 211.

Further, once production of a mask pack is started, then the base 210 of the platform 200 is ascended or descended along the z-axis by the z-axis linear driving device 221, and thanks to roles or functions of the film holder 230, the peripheral stepped portion 212 and the film seat portion 211, such an accident as the separation of the film 20 from the platform 200 during the operation of the device 10 for producing a skin care pack using hydrogel of the embodiment cannot consequently occur.

At the time of removing the film 20, a user can the film holder 230 from the base 210, and then puts his/her hand toward the film removal recessed portion 213 and easily removes the film 20 by pulling it.

FIG. 6 is a perspective view showing the former shown in FIG. 2; and FIG. 7 is an exploded perspective view of the former shown in FIG. 6. Further, FIG. 8 is a front view of the nozzle module disposed at a right side of the discharge unit of the former shown in FIG. 7; and FIG. 9 is a cross-sectional view taken along line B-B shown in FIG. 8.

Referring to FIGS. 6 to 9, the former 300 may include the two y-axis linear driving devices 321, 322 and the one x-axis linear driving device 323, which are controlled by the control unit 400 as described above so as to operate in linkage with the platform 200. These linear driving devices 321, 322, 323 may be linear motors.

For example, the two y-axis linear driving devices 321, 322 may be parallelly disposed on the floor plate 102 of the housing 100 except an area where the platform 200 is installed. As the two y-axis linear driving devices 321, 322 are parallelly disposed, the payload of the x-axis linear driving device 323 and inertial force caused by its movement can be stably supported, so that the mask pack production can be precisely performed.

Also, the former 300 may include two adapter blocks 324, 325 combined to moving plates of the y-axis linear driving devices 321, 322, respectively.

In addition, the x-axis linear driving device 323 may be installed between the adapter blocks 324, 325 so as to be supported by the adapter blocks 324, 325. In this case, a universal adapter plate 326 may be interposed between the adapter blocks 324, 325 and a body case of the x-axis linear driving device 323 for installing an additional equipment such as a cable guide or the like. As the universal adapter plate 326 is provided with a plurality of installation holes, it is advantageously possible to endow the x-axis line driving device 323 with degree of freedom for mounting.

Like this, the linear driving devices 221, 321, 322, 323 are configured to be separated into two axes (e.g., x-y axis) and one axis (e.g., z axis), and thus it can stably produce 3D skin care pack or mask pack while relatively increasing accuracy of repeated movement of the discharge unit H.

Further, the former 300 may include a T-shaped mount block 327 combined to a moving plate of the x-axis linear driving device 323, and one or more nozzle modules 310, 350 fixed to a front surface of the mount block 327. At each nozzle module 310, 350, a pressure sensor (not shown) may be further installed for sensing installation or replacement of the syringe 312. At this time, the pressure sensor may be electrically connected to the control unit 400.

In the embodiment, the two nozzle modules 310, 350 are described by way of example as being fixed to both sides of the front surface of the mount block 327.

As the discharge unit H of the former 300, these nozzle modules 310, 350 may be configured to satisfy requirements of a hydrogel discharge device. Here, the requirements of the hydrogel discharge device may mean convenience of charging and replacing a raw material, heating performance of a syringe, a tube and a nozzle for melting the hydrogel, extrusion performance of a fixed amount of the hydrogel, and maintenance convenience (e.g., cleansing and nozzle replacement).

The nozzle modules 310, 350 are configured to be fixed to the mount block 327 and moved together with the mount block 327.

Further, the nozzle modules 310, 350 are symmetrically arranged on both sides with respect to the front surface of the mount block 327 to discharge toward the platform 200 the hydrogel as a raw material for producing a mask pack.

Here, each nozzle module 310, 350, and the mount block 327 may be connected to each other through an angle member 328 of an L-shaped cross section. Due to use of the angle member 328, it can become very easy to install, separate each nozzle module 310, 350, and perform maintenance thereon.

Also, the former 300 may further include a finishing member 329. Here, the finishing member 329 may be a lightweight metallic or non-metallic metal material, and be combined to a lower surface of the mount block 327 for a finishing treatment of the angle member 328 disposed between the nozzle modules 310, 350.

More specifically, the finishing member 329 may include a fixing plate 329a and a finishing plate 329b, which are integrally formed. The fixing plate 329a of the finishing member 329 may contact the lower surface of the mount block 327 and be fixed to the mount block 327 through bolt fastening to bolt holes formed correspondingly to each other. The finishing plate 329b of the finishing member 329 may be extended from the fixed plate 329a so as to have a C-shaped cross section, so that it can be disposed between the nozzle modules 310, 350 while covering a front position of the angle member 328 in a non-contact manner. In other words, the finishing member 329 can perform a role of protecting and a role of aesthetically finish treating the angle member 328, that is, a position where the nozzle modules 310, 350 are fixed.

Each of the nozzle modules 310, 350 may include a syringe 312, a nozzle 311 and a pump 340. Here, the nozzle 311 and the pump 340 may include thermally conductive metal as their material, so that they can be heated by heat conduction transferred through the main block 330.

As the nozzle 311 is provided to each nozzle module 310, 350, relatively more amount of the raw material can be discharged, so it is possible to relatively rapidly produce a skin care pack.

Further, as the nozzle modules 310, 350 may be provided left-right symmetrically, hereinafter the detailed configuration thereof will be explained focused on the nozzle module 310 located right in FIG. 6 in order to avoid repeated explanation.

Referring to FIGS. 8 and 9, the nozzle module 310 may be configured to perform ultra-precise fixed amount raw material discharge, to be capable of continuously discharging a raw material while satisfying heat requirements suitable to properties of the raw material, such as the hydrogel or the like, and not to leak a raw material of a low viscosity through the nozzle 311, so that a mask pack can be rapidly and accurately produced.

Specifically, the nozzle module 310 may include the syringe 312 which stores a raw material, and the main block 330.

First, the syringe 312, which is a replaceable cartridge capable of being attached to or detached from the nozzle module 310, corresponds to a raw material storage means.

Further, the nozzle 311 of the nozzle module 310 is disposed spaced apart under the syringe 312. In this case, the nozzle 311 is detachably combined to a raw material discharge hole of the main block 330. If a hole of the nozzle 311 is clogged, or if its replacement is needed, the nozzle 311 may be detached from the raw material discharge hole of the main block 330 by a user or a maintenance worker.

The main block 330 may be disposed between the nozzle 311 and the syringe 312, become a support base of the nozzle 311, the syringe 312 and the angle member 328, and provide a raw material flow path 331.

The nozzle module 310 includes the pump 340 which is installed to the main block 330 so as to be communicated to the raw material flow path 331, and which pumps a raw material of the syringe 312 to supply the same toward the nozzle 311. The pump 340 may be connected to the main block 330 through a pump bracket 349, and receive heat transfer from the main block 330 or a heater 332.

That is, the raw material flow path 331 may be heated by the heater 332. Further, the control unit 400 may control the heater 332 so that temperature of the main block 330 measured by a temperature sensor 333 to be described below can be maintained to a predetermined range.

Further, heat of the heater 332 may be transferred to a tube 341 of the pump 340, the nozzle 311, and a syringe heating block 334 through the main block 330 to which the one heater 332 is installed. Therefore, temperature of the hydrogel, a raw material, can be stably maintained to a requirement value necessary for skin care pack production, and heat transfer efficiency can be maximized.

The pump 340 may be a peristaltic pump, so that a raw material which is heated by the heater 332 can satisfy the above-described hydrogel discharge device requirements without being leaked from the nozzle 311. If the peristaltic pump is used as the pump 340, there is no cross contamination between a raw material to be discharged and the pump 340, complete self-priming pumping operation thereof is possible, and safe run-dry is possible without any damage to the pump 340. Further, neither a valve nor a seal is necessary, and pumping operation is smooth. Thus, the hydrogel which is sensitive to deformation can be smoothly discharged.

Further, the temperature sensor 333 and the heater 332 for generating heat corresponding to heating conditions of a raw material or providing such heat to a raw material may be installed to the main block 330.

The heater 332 basically heats the main block 330 and various constituting elements connected to the main block 330. For example, the heater 332 may perform heating operation to a temperature of the heating conditions (e.g., 70° C. to 95° C.) for decreasing viscosity of a raw material for a mask pack production, such as hydrogel, on entire regions of an extruding section, such as the main block 330, the nozzle 311, the tube 341 of the pump 340, the syringe heating block 334 and the syringe 312. The main block 330 may be formed with thermally conductive material (e.g., metallic material).

For example, the heater 332 may be configured to heat the syringe heating block 334, the main block 330, the syringe 312, the nozzle 311 and the nozzle joint 311. Thanks to this, heat can be preserved in a rear portion of the syringe 312 in which a raw material is contained and a conveying section of a raw material, so that optimized viscosity can be maintained.

If a raw material is heated to a temperature of the heating condition or lower via the heater 332, it is difficult to perform conveying action for extrusion because of high viscosity, whereas if it is heated to a temperature of the heating condition or higher, there may occur degraded extrusion because air bubbles are generated due to evaporation of moisture of a raw material.

The main block 330 is disposed at a central position of three directions with regard to the syringe 312, the nozzle 311 and the pump 340 which are connected to the main block 330 in each of the directions. Specifically, the syringe 312 is disposed above the main block 330 in the gravity direction; the pump 340, at a side of the main body in a lateral one side; and the nozzle 311, below the main block in the gravity direction. Therefore, heat of the main block 330 can be transferred evenly to the syringe 312, the nozzle 311 and the pump 340.

In particular, as a highest temperature ambience is formed at a lower side of the syringe 312 by the heater 332, the hydrogel which is contained in the syringe 312 at a low viscosity also forms a highest temperature ambience at the lower side of the syringe 312. Due to this, convection currents occur in the hydrogel within the syringe 312, by which the entire hydrogel in the syringe 312 has a similar heating state. Therefore, the viscosity of the hydrogel discharged through the syringe 312 can be maintained uniform, and thereby quality of forming a mask pack and quality of a final product can be improved.

Further, as the temperature sensor 333 is installed in the main block 330 with respect to a position adjacent the heater 332, a temperature value which is measured through the temperature sensor 333 and input toward the control unit 400 can be used relatively precisely to perceive the heating condition of a raw material.

Meanwhile, the raw material flow path 331 of the main block 330 may be configured to turn the raw material discharged from the upper side syringe 312 to a side direction and transfer the same toward the pump 340 side, and turn the raw material discharged from the lateral side pump 340 to a downward direction and turn the same to the nozzle 311, and be connected to the U-shaped flexible tube 341 of the pump 340.

There may be provided quick couplers for tube piping at connection points between both ends of the tube 341 and the raw material flow path 331, and thus it is possible to easily replace the tube 341.

The tube 341 may be installed at the pump 340 with respect to a gap between a plurality (e.g., ten) of rollers 342, 343 of the pump 340 and a tube housing 344 so that it can be pressed to be deformed or restored by the rollers 342, 343 of the pump 340. The tube housing 344 may have structure in which it can be attached or detached with a bolt (not shown).

The pump 340 includes a pump head which is driven by a pump motor (not shown), and the plurality of rollers 342, 343 rotatably disposed along a circumferential direction of the pump head.

The rotation and revolution of the rollers 342, 343 may press the tube 341 in a diameter direction of the tube 341, and as a result, inner surfaces of the pressed tube 341 may be brought into close contact with each other, so that movement of a raw material in the tube 341 can be blocked. When the pump head is rotated by the pump motor of the pump 340, the rollers 342, 343 may be moved correspondingly to the rotation of the pump head. As the rollers 342, 343 are moved, suction of the raw material is accomplished by a negative pressure generated in the tube 341 when the tube 341 is restored to its original shape.

That is, as a raw material as much as a flow rate corresponding to a space between the rollers 342, 343 is repeatedly collected in the tube 341, the conveyance of the raw material can be accomplished from the inside of the syringe 312 to the nozzle 311 by way of the raw material flow path 331 of the main block 330 and the tube 341.

A syringe joint 380 may be installed between an upper surface hole of the raw material flow path 331 of the main block 330 and the syringe 312. In this case, for the purpose of easiness of replacement of the syringe 312, an upper end of the syringe joint 380 may be screw-coupled to the syringe 312 so as to be assembled or disassembled, while a lower end of the syringe joint 380 may be screw-coupled to the upper surface hole of the raw material flow path 331 of the main block 330.

Further, a nozzle joint 381 may be installed between a lower surface hole of the raw material flow path 331 of the main block 330 and the nozzle 311. In this case, for the purpose of easiness of replacement of the nozzle 311, an upper end of the nozzle joint 381 may be screw-coupled to a lower surface hole of the raw material flow path 331 of the main block 330, while a lower end of the nozzle joint 381 may be coupled with the nozzle 311 in a simple press-fit manner. Therefore, if the replacement of the nozzle 311 is needed, a user may extract the nozzle 311 from the nozzle joint 381, and insert a new nozzle (not shown) into the nozzle joint 381.

Meanwhile, the nozzle module 310 may include the syringe heating block 334 which is extended upward from an upper surface periphery of the main block 330, and which has a first semi-circular recessed portion in contact with an outer circumferential surface of a side of the syringe 312. Further, the nozzle module 310 may include a syringe cover block 335 which is disposed opposite the syringe heating block 334 with respect to the syringe 312, and which has a second semi-circular recessed portion in contact with an outer circumferential surface of another side of the syringe 312.

The syringe cover block 335 and the syringe heating block 334 form a syringe insertion hole therein with the first and second semi-circular recessed portions, and the syringe 312 may be inserted through or separated from the syringe insertion hole. As a result, the replacement of the syringe 312 can be performed easily and rapidly. Here, the syringe cover block 335 may be formed with a Teflon material having a low thermal conductivity. By this, the heat inside the syringe 312 can be well-preserved.

Also, a slit 336 for checking raw material remainder quantity in the syringe 312 is formed in the syringe cover block 335 so as to penetrate the syringe cover block 335 in a thickness direction. Since a casing of the syringe 312 is a transparent or semi-transparent material, a user can intuitively check the remainder quantity of a raw material in the syringe 312 with user's naked eyes, and the slit 336 can provide excellent visibility to a user.

Hereinafter, operation and effects of the device 10 for producing a skin care pack using hydrogel according to an embodiment having a configuration as described above will be described.

That is, the embodiment has an effect that a custom-tailored skin care pack using hydrogel as a raw material can be produced or manufactured rapidly. Further, according to the embodiment, there is an advantage of producing a skin care pack rapidly and precisely even though using hydrogel as a raw material. In addition, with the configuration where the heat transfer efficiency can be maximized thanks to the provision of the main block 330 which can be heated by heat of the one heater 332, the heat of the heater 332 can be transferred to the tube 341 of the pump 340, the nozzle 311, and the syringe heating block 334 through the main block 330, and thus there is an effect that the temperature of the hydrogel which is a raw material can be stably maintained to a requirement value necessary for producing a skin care pack. As a result, it is possible to produce a high quality hydrogel skin care pack.

Hereinafter, a method of washing the producing device 10 according to the embodiment will be described with reference to drawings.

FIG. 10 is a flowchart for explaining a washing process, which is a control method of the device for producing a skin care pack using hydrogel according to the invention.

Referring to FIG. 10, if the syringes installed at the right nozzle module 310 and the left nozzle module 350 are referred to as a first syringe and a second syringe, respectively, when the use of the first and the second syringes has been completed, or when washing for the nozzle is necessary due to non-use of the device for a long time, the first and second syringes whose use has been completed may be removed or separated from the syringe heating blocks 334 that are installed at the nozzle blocks 310, 350, respectively (S110). In the embodiment, the two syringes are described by way of example as being replaced or removed simultaneously, but only any one of them may be replaced or removed. In this case, the other syringe may maintain the state of being installed at the nozzle module as it is.

And, new third and fourth syringes may be installed at the syringe heating blocks 334, respectively (S120).

After the step (S120) of installing the third and fourth syringes, the control unit 400 may perform a step of receiving an input of a washing instruction (not shown).

For example, the washing instruction may be input by a user through a user interface means, such as the aforementioned input/output display device, or the washing instruction may be automatically input by means of sensing the installation of the third and fourth syringes which are new syringes.

The control unit 400 may control the pumping operation of the pumps 340 mounted on the nozzle modules 310, 350, respectively in such a manner that hydrogel of the third and fourth syringes to the nozzles 311 can be supplied to the nozzles 311, and that the hydrogel stayed in the nozzles 311, the raw material flow paths 331, the tubes 341 and the like which has been discharged from the first and second syringes can be discharged therefrom while at the same time the inside of the nozzles 311, the raw material flow paths 331, the tubes 341 and the like can be replaced with the hydrogel which is supplied from the new third and fourth syringes (S130).

With regard to such replacement step (S130), the control unit may perform a step of driving the pump 340 until the timing when the hydrogel of the new syringe is discharged through the nozzle 311 on the basis of information calculated according to a structural characteristic of a path through which hydrogel is moved in the nozzle modules 310, 350 and operation condition of the pump 340. Here, the timing of being discharged through the nozzles 311 may be one when a predetermined amount (e.g., very small amount) of a new hydrogel is discharged. The control unit 400 may stop the operation of the pump 340 based on the timing when the hydrogel is discharged out of the nozzle by replacing like this (S140).

In this case, the control unit 400 may calculate the operation condition of the pump 340 of until the hydrogel newly discharged from the third and fourth syringes is discharged to the nozzle 311 using the predetermined structure of the nozzle 311, the raw material flow path 331, the tube 341 and the like, and the thus calculated operation condition may be stored in a memory (not shown) and used as needed. At this time, the control unit 400 may stop the pump 340 after its reverse rotation operation in order to prevent the hydrogel stayed in the nozzle 311 from dropping out of the nozzle 311 due to decrease in viscosity (S150).

According to the washing method according to an embodiment of the invention as described above, in a state where the syringe has been replaced, the replacement by a new nozzle (not shown) is unnecessary, and it is possible to completely remove micro air bubbles which may flow into the raw material flow path 331 or the tube 341 due to the syringe replacement. So, there is an advantage that it is possible to form a high quality mask pack.

Hereinafter, a configuration of a device for producing a skin care pack using hydrogel according to an application example of the invention will be described.

FIG. 11 is a perspective view of a dual nozzle module of a device for producing a skin care pack using hydrogel according to an application example of the invention; FIG. 12 is a perspective view for describing operational relation of the dual nozzle module shown in FIG. 11; and FIG. 13 is a flowchart for explaining a control method of the dual nozzle module shown in FIG. 12.

Referring to FIGS. 11 to 13, a former according to the application example of the invention may include a dual nozzle module 360 which may be controlled by a control unit to operate in linkage with a platform, and which may be moved or stopped by a y-axis linear driving device and an x-axis linear driving device.

The dual nozzle module 360 includes two syringes 312, one nozzle 361 and two pumps 340, 345.

Each pump 340, 345 includes a tube housing 344*a* which can be opened and closed in a hinge manner. A one side end of each tube housing 344*a* may be a hinge 344*b* positioned under a pump body, and another end of the tube housing 344*a* may be a U-shaped fastening end portion 344*c* which can be bolt-coupled to a fastening hole positioned at an upper side of the pump body.

Therefore, if a maintenance worker removes a corresponding bolt (not shown), each tube housing 344*a* can be rotated with respect to the hinge 344*b*, and as a result a tube is exposed, so that maintenance of the tube can be easily accomplished.

Such dual nozzle module 360 serves as a role of discharging through the one nozzle 361 a raw material for forming a mask pack.

Specifically, a dual heating block 370 may be mounted on the dual nozzle module 360. The tube of each of the two pumps 340, 345 is connected to a raw material flow path 331*a*, 331*b* for each of the syringes 312, and the raw material flow paths 331*a*, 331*b* are formed in the dual heating block 370.

Further, a raw material mixing path 331*c* is formed in the dual heating block 370 in relation to exit sides of the raw material flow paths 331*a*, 331*b*. The one nozzle 361 is penetratingly piped to the raw material mixing path 331*c*. The one nozzle 361 may discharge raw materials for producing different kinds of skin care packs in a mixing state, which enables the production of various functional skin care pack.

Further, a heater 332 and a temperature sensor 333 connected to the control unit are installed in the dual heating block 370, and the heater 332 may heat the syringes 312 disposed at an upper side, the pumps 340, 345 disposed at a side, and a nozzle 361 disposed at a lower side such that the hydrogel can be discharged under a heating condition as in said embodiment. The heating temperature of the dual heating block 370 may be determined within a predetermined temperature range. Further, as the heating temperature of the dual heating block 370 may be changed depending on a size and material of the dual heating block 370, if it is a temperature selected within a temperature range for forming a target viscosity for the hydrogel which corresponds to a mixed material, it may not be limited to a specific temperature value.

As the first pump 340 and the second pump 345 of the dual nozzle module 360 operate, raw materials corresponding to different or same pumping flow rate may be supplied from the two syringes 312 to the raw material mixing path 331c, and mixed with each other therein to make a mixed raw material. Such mixed raw material is discharged toward the platform by being discharged through the one nozzle 361 which is penetratingly connected to the raw material mixing path 331c. That is, the mixed raw material may be discharged onto a film of the platform through the nozzle 361 so as to make a pattern portion corresponding to a mask pack.

Referring to FIG. 13, according to a control method of the device for producing a skin care pack using hydrogel according to an application example, if the former which is moved by the x-axis and y-axis linear driving devices includes the dual nozzle module 360, a step of installing a plurality of syringes at the dual heating block 370 to which the first pump 340 and the second pump 345 of the dual nozzle module 360 are combined may be accomplished (S210).

After this, the control unit may perform a step of receiving a setting of a hydrogel supply ratio for each syringe (S220). Step S220 may be performed by receiving an input of predetermined data from a user by a user interface means, such as the above-described input/output display device, or by reading data which have been stored in advance in a memory according to a kind of the raw material or the like.

And, the control unit may control the temperature of the dual heating block 370 within a temperature range corresponding to a heating condition of a mask pack forming by activating the heater installed in the dual heating block 370 (S230).

In the embodiment, while the step S220 has been described by way of example as being performed before the step S230, the order of two steps is not limited to this.

After this, the control unit supplies the hydrogel toward the dual heating block 370 by controlling each pumping flow rate of the first and second pumps 340, 345 correspondingly to the supply ratio (S240).

Hydrogels of different kinds which have been conveyed from tubes of the first and second pumps 340, 345, respectively may be mixed with each other on the raw material mixing path 331c of the dual heating block 370, and be discharged through the one nozzle 361 (S250).

According to the device for producing a skin care pack using hydrogel according to the application example of the invention as described above, by mixing hydrogels, which are different from each other and stored in the plurality of syringes, respectively, and discharging the same through the one nozzle 361, an effect of being capable of producing a skin care pack with hydrogels of component ratios that a user wants is exhibited.

While until now the device for producing a skin care pack using hydrogel according to examples of the invention has been described as concrete embodiments, these are just exemplary embodiments, and the present invention should be construed in a broadest scope based on the fundamental technical ideas disclosed herein, rather than being limited to them. By combining or replacing a part or parts of embodiments disclosed herein, the ordinary skilled in the art may carry out a pattern of a shape which is not explicitly described herein, and however, it should be noted that it shall not depart from the scope of the invention. Besides, the ordinary skilled in the art may easily change or modify embodiments disclosed herein based on the disclosure, and however, it is obvious that such change or modification also falls within the scope of the invention.

INDUSTRIAL APPLICABILITY

The invention can be used in the cosmetics industry.

The invention claimed is:

1. A device for producing a skin care pack using hydrogel, the device comprising:
    a housing which is provided with a door for selectively opening and closing a work space for forming a skin care pack, and which maintains a forming temperature required for producing the skin care pack;
    a platform having a base supported on a floor plate of the work space of the housing;
    a former including one or more nozzle modules which are provided to be movable in the work space, and which heat the hydrogel and discharge same onto the platform; and
    a control unit for controlling movement of the nozzle modules and discharge of the hydrogel from the nozzle modules,
    wherein an individual nozzle module of the nozzle modules includes:
        a main block which includes a heater, and which is formed of a thermally conductive material;
        a syringe which is installed at the main block, and which stores the hydrogel;
        a nozzle which is installed at the main block, and which discharges the hydrogel onto the platform; and
        a pump which is installed at the main block, and which supplies the hydrogel from the syringe to the nozzle, and
    wherein the platform includes:
        a z-axis linear driving device which is driven according to a control signal supplied by the control unit, and which is installed on the floor plate of the housing;
        a base which is ascended or descended along a z-axis direction by the z-axis linear driving device, which is disposed above a driving device protection cover of the work space of the housing, and which has a plurality of film seat portions partitioned by a peripheral stepped portion so that a pattern part constituting a mask pack are dividedly formed into a plurality of pieces; and
        a plurality of film holders which are attached to or detached from the peripheral stepped portion of the base by a means of magnetic force.

2. The device according to claim 1, wherein the door is hinge-combined to a ceiling wall of the housing, and there is provided a tension gas spring between the door and a side wall of the housing.

3. The device according to claim 1, wherein the housing includes the driving device protection cover which is installed on the floor plate of the housing so as to cover a lower portion of a linear driving device of the platform or a lower portion of a linear driving device of the former, and wherein the driving device protection cover is provided to be capable of being assembled or disassembled for installation and maintenance of the platform or the former.

4. The device according to claim 3, wherein a residue collecting receptacle for collecting residues which are generated when washing the nozzle of the former is detachably installed at a front portion of the driving device protection cover.

5. The device according to claim 1, wherein the hydrogel stored in the syringe receives heat transferred from the heater, so that its viscosity is maintained between 120 CPS and 2,500 CPS.

6. The device according to claim 1, wherein the syringe, the nozzle, and the pump are heated by heat transferred to themselves from the heater.

7. The device according to claim 6, wherein the nozzle and the pump include thermally conductive metal as a material so that they can be heated by heat conduction transferred to themselves through the main block.

8. The device according to claim 6, wherein the syringe is disposed at a gravity-direction upper side of the main block, the pump is disposed at a lateral one side of the main block, and the nozzle is disposed at a gravity-direction lower side of the main block.

9. The device according to claim 6, wherein the heater heats the syringe, the nozzle and the pump so that viscosity of the hydrogel discharged from the nozzle is maintained between 120 CPS and 2,500 CPS, or so that temperature of the hydrogel is maintained between 70° C. and 95° C.

10. The device according to claim 6, wherein the main block includes a raw material flow path which provides to the pump the hydrogel supplied from the syringe, and which provides to the nozzle the hydrogel supplied from the pump, and the raw material flow path is heated by the heater.

11. The device according to claim 1, wherein the main block is further provided with a temperature sensor for sensing temperature of the main block, and the control unit controls the heater so that temperature of the main block measured at the temperature sensor is maintained to a predetermined temperature range.

12. A device for producing a skin care pack using hydrogel, the device comprising:
a housing which is provided with a door for selectively opening and closing a work space for forming a skin care pack, and which maintains a forming temperature required for producing the skin care pack;
a platform having a base supported on a floor plate of the work space of the housing;
a former including one or more nozzle modules which are provided to be movable in the work space, and which heat the hydrogel and discharge same onto the platform; and
a control unit for controlling movement of the nozzle modules and discharge of the hydrogel from the nozzle modules,
wherein an individual nozzle module of the nozzle modules includes:
a main block which includes a heater, and which is formed of a thermally conductive material;
a syringe which is installed at the main block, and which stores the hydrogel;
a nozzle which is installed at the main block, and which discharges the hydrogel onto the platform;
a pump which is installed at the main block, and which supplies the hydrogel from the syringe to the nozzle,
a syringe heating block which is extended upward from an upper surface periphery of the main block, and which has a first semi-circular recessed portion in contact with an outer circumferential surface of a side of the syringe; and
a syringe cover block which is disposed opposite the syringe heating block with respect to the syringe, and which has a second semi-circular recessed portion in contact with an outer circumferential surface of another side of the syringe.

13. The device according to claim 12, wherein a slit for checking a raw material remainder quantity of the syringe is formed in the syringe cover block.

14. The device according to claim 1,
wherein the plurality of film holders include:
a pad which contacts an upper surface of a film and the peripheral stepped portion of the base in order to prevent scratch generation resulting from the contact with the film placed on the film seat portions;
a handle connected to a top of the pad; and
a magnet disposed in the handle with respect to an upper side position of the pad.

15. The device according to claim 1,
wherein the former includes:
two y-axis linear driving devices which are parallelly disposed on the floor plate of the housing except an installation area of the platform;
two adapter blocks combined to moving plates of the y-axis linear driving devices, respectively;
an x-axis linear driving device installed between the adapter blocks; and
a mount block combined to a moving plate of the x-axis linear driving device, and
wherein the nozzle modules are fixed to the mount block and moved together with the mount block.

16. The device according to claim 15, wherein the mount block has a shape of T, and the nozzle modules are symmetrically disposed at both sides of the mount block.

17. The device according to claim 16, wherein the nozzle modules and the mount block are connected to each other through an angle member of an L-shaped cross section,
the former further includes a finishing member which is combined to a lower surface of the mount block for a finishing process of the angle member disposed between the nozzle modules, and
the finishing member includes:
a fixed plate in contact with the lower surface of the mount block; and
a finishing plate which is extended from the fixed plate so as to have a C-shaped cross section, so that it is disposed between the nozzle modules while covering a front position of the angle member.

* * * * *